United States Patent [19]

Barriere et al.

[11] Patent Number: 5,789,537
[45] Date of Patent: Aug. 4, 1998

[54] METHOD FOR PREPARING STREPTOGRAMINS

[75] Inventors: Jean-Claude Barriere, Bures Sur Yvette; Luc Grondard, Courcouronnes; Patrick Lefevre, Courbevoie; Stéphane Mutti, Le Perreux Sur Marne, all of France

[73] Assignee: Rhône-Poulenc Rorer S.A., Antony Cedex, France

[21] Appl. No.: 930,135

[22] PCT Filed: Apr. 16, 1996

[86] PCT No.: PCT/FR96/00575

§ 371 Date: Oct. 16, 1997

§ 102(e) Date: Oct. 16, 1997

[87] PCT Pub. No.: WO96/33213

PCT Pub. Date: Oct. 24, 1996

[30] Foreign Application Priority Data

Apr. 18, 1995 [FR] France ................... 95 04585

[51] Int. Cl.$^6$ ................................................ C07K 5/00
[52] U.S. Cl. ............................................... 530/317
[58] Field of Search ........................ 530/317; 514/11

[56] References Cited

U.S. PATENT DOCUMENTS 5,310,900  5/1994  Barriere et al. ............... 540/455
5,637,565  6/1997  Anger et al. .

FOREIGN PATENT DOCUMENTS

A-2689518  10/1993  France .

OTHER PUBLICATIONS

Derwent Abstract of FR–A–2689518.
Takata et al., "Mild and Selective Oxygen Atom Transfer: $^nBu_4NIO_4$ with Metalloporphyrins," Tetraheron Letters, 24(34):3631–3634 (1983).

*Primary Examiner*—Raymond Henley, Jr.
*Attorney, Agent, or Firm*—Finnegan, Henderson, Farabow, Garrett & Dunner, L.L.P.

[57] ABSTRACT

A method for preparing streptogramins of the formula (I):

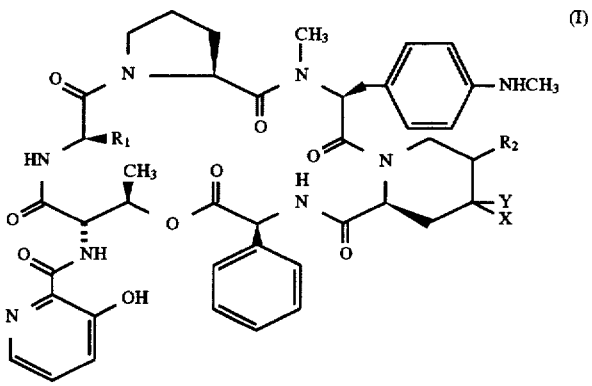

wherein $R_1$ is methyl or ethyl, $R_2$ is H and X and Y together form an oxo radical, or $R_1$ is ethyl, $R_2$ and X are H and Y is H or OH, or else $R_1$ is ethyl, $R_2$ is OH and X and Y together form an oxo radical, by demethylation of a synergistin derivative of the formula (II):

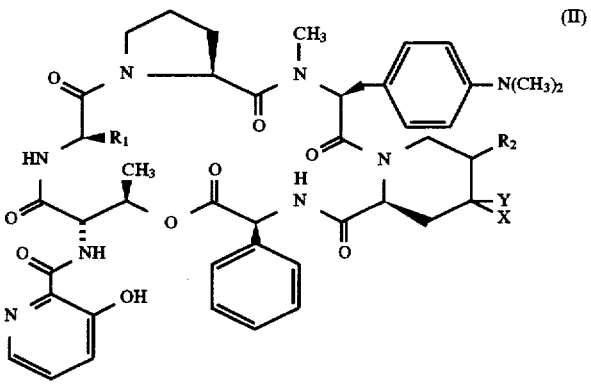

wherein $R_1$, $R_2$, X and Y are as defined above, by means of a treatment with a periodate in an acetic medium, followed by a treatment in an aqueous medium.

6 Claims, No Drawings

METHOD FOR PREPARING STREPTOGRAMINS

This application is a 371 of PCT/FR 96/00575 filed Apr. 16, 1996.

The present invention relates to a novel process for the preparation of streptogramins of general formula:

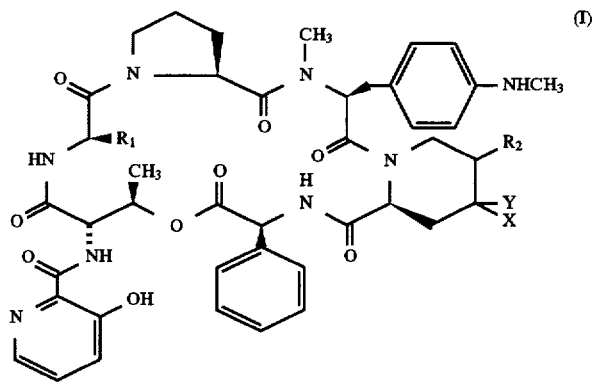

(I)

in which:
either the radical $R_1$ represents a methyl or ethyl group, the radical $R_2$ represents a hydrogen atom and X and Y together form an oxo radical,
or $R_1$ represents an ethyl radical, $R_2$ and X represent a hydrogen atom and Y represents a hydrogen atom or a hydroxyl radical,
or $R_1$ represents an ethyl radical, $R_2$ represents a hydroxyl radical and X and Y together form an oxo radical,
from a synergistin derivative of general formula:

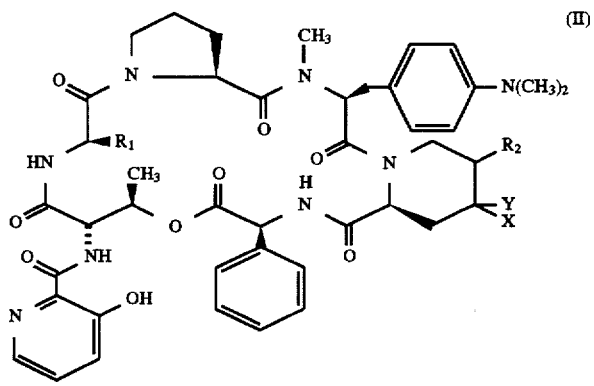

(II)

in which the radicals $R_1$, $R_2$, X and Y are as defined above.

Streptogramins are a known class of compounds comprising components of group B [to which the products of general formula (I) belong] which, when combined with components of group A, bring about a synergism of the antimicrobial action.

The product of general formula (I) for which $R_1$ is ethyl and $R_2$ is hydrogen is known under the name of pristinamycin IB. The product of general formula (I) for which $R_1$ is methyl and $R_2$ is hydrogen is known under the name of vernamycin Bδ. The product of general formula (II) for which $R_1$ is ethyl and $R_2$ is hydrogen is known under the name of pristinamycin IA. The product of general formula (II) for which $R_1$ is methyl and $R_2$ is hydrogen is known under the name of pristinamycin IC or vernamycin Bγ. The product of general formula (II) for which $R_1$ is ethyl and $R_2$ is hydroxyl is known under the name of pristinamycin ID.

General methods of demethylation were already known, for example such as the methods described in Tet. Lett., 18, 1567 (1977); J. Org. Chem., 49, 2795 (1984); J. C. S. Chem. Comm., 905 (1989), Tet. Lett., 33, 6991 (1992); however, these methods could not be adapted to fragile products such as streptogramins, either because the reaction did not take place or because the operating conditions were degrading towards these products. Yet other methods involved toxic reactants which were not totally removable from the final product, this being unacceptable from the pharmaceutical point of view.

It has now been found, and this forms the subject of the present invention, that the streptogramins of general formula (I) could be obtained by demethylation of the corresponding derivative of general formula (II) by treatment with a periodate in acetic medium followed by a treatment in aqueous acidic medium or by a treatment with an agent capable of consuming the formaldehyde in situ.

The periodate used is advantageously tetra-n-butylammonium periodate or an alkaline periodate (sodium periodate). The reaction is carried out in a solvent such as a chlorinated solvent (for example dichloromethane, chloroform, dichloroethane or trichloroethane), an ester (for example ethyl acetate), a nitrile (for example acetonitrile) or in tetrahydrofuran, N-methylpyrrolidone or optionally a mixture of these solvents, in the presence or absence of ethylene glycol. The reaction takes place at a temperature of between 20° and 40° C.

The subsequent treatment is a hydrolysis, in aqueous medium, which releases formaldehyde. It is possible to perform the process by treatment of the product obtained in a homogeneous aqueous medium to which is added a strong acid, or directly in an acidic or non-acidic two-phase medium; in particular, the process may be performed in a dichloromethane/water mixture. In this case, preferably, the pH of the aqueous medium will be weakly acidic; it is understood that the acidity of the medium will be provided, indiscriminately, by addition of a strong or weak acid.

The acids used may be chosen in particular from trifluoroacetic acid, sulphuric acid, hydrochloric acid, methanesulphonic acid, p-toluenesulphonic acid or formic acid. The treatment in acidic medium is carried out at a temperature of between 0° and 40° C.

When the subsequent treatment is carried out, it is also possible further to add an agent capable of consuming the formaldehyde in situ, this agent is advantageously chosen from hydroxylamine, a bisulphite (for example sodium bisulphite) or hydrogen peroxide in aqueous medium. The process is preferably performed in a two-phase medium at a temperature of between 0° and 40° C., at a pH of between 1 and 7.

The products of general formula (I) thus obtained may be purified, where appropriate, by the usual methods such as crystallization, precipitation, flash chromatography or HPLC.

The products of general formula (I) in which $R_1$ represents an ethyl radical, $R_2$ and X represent a hydrogen atom and Y represents a hydrogen atom or a hydroxyl radical are novel products of the streptogramin family.

The examples which follow, given without any limitation being implied, illustrate the process according to the invention.

EXAMPLE 1

540 g of crude pristinamycin I [pristinamycin $I_A$ 72.2% (433 g), pristinamycin $I_B$ 4.2% (25 g), pristinamycin $I_C$ 2.67% (16 g), pristinamycin $I_D$ 3.17% (19 g)] are placed in solution in a mixture of 1460 cm³ of dichloromethane, 500 cm³ of acetic acid and 40 cm³ of ethylene glycol, in a three-necked flask. 97.5 g of tetra-n-butylammonium periodate are added, while maintaining the temperature at 30° C. After stirring for 3 hours at 30° C., the reaction is stopped by addition, with stirring, of 2000 cm³ of demineralized water. The aqueous phase is separated out by settling and the organic phase is washed again with 2000 cm³ of demineralized water. The aqueous phase is separated out by settling and the organic phase is concentrated to a volume of 800 cm³. 1000 cm³ of methyl ethyl ketone are added to the concentrate and the mixture is concentrated under reduced pressure (1.5 kPa) to a volume of 1300 cm³. Methyl ethyl ketone is added up to a total volume of 2400 cm³ and the mixture is cooled to 0° C. The precipitated solid is filtered off, washed with 3 times 250 cm³ of methyl ethyl ketone and then dried at 40° C. under reduced pressure (1.5 kPa). 441 g of a white solid are thus obtained, which product is dissolved in 8800 cm³ of 0.25N hydrochloric acid and stirred for 1 hour and then extracted with 3500 cm³ of dichloromethane, adjusting the pH of the aqueous phase to 4 with 30% sodium hydroxide. The organic phase is separated out by settling, washed with 3500 cm³ of water and then concentrated to dryness under reduced pressure (50 kPa at 30° C.) to a volume of about 1100 cm³. 2200 cm³ of ethanol are added to this solution and the evaporation under reduced pressure is continued down to 1800 cm³. 3500 cm³ of ethanol are then added. The crystals obtained are filtered off at 10° C., filtered off and then rinsed with 3 times 330 cm³ of cold ethanol, then dried at 40° C. under reduced pressure (1.5 kPa). 360 g of pristinamycin $I_B$ are thus obtained in the form of white, 80.7% pure crystals, i.e. containing 290.4 g of pristinamycin $I_B$.

Moreover, 1.1% of vernamycin Bδ was obtained, equivalent to a conversion yield of 41.2%, and 2% of pristinamycin of general formula (I) in which $R_1$ is ethyl and $R_2$ is hydroxyl, equivalent to a conversion yield of 63% (HPLC assay).

EXAMPLE 2

20 g of pristinamycin I [pristinamycin $I_A$ 76.5% (15.3 g), pristinamycin $I_B$ 7% (1.4 g)] are placed in solution, in a three-necked flask, in a mixture of 28 cm³ of 1,2-dichloroethane, 70 cm³ of acetic acid and 2 cm³ of ethylene glycol. 4.9 g of sodium periodate are added, while maintaining the temperature at 25° C. After stirring for 6 hours, the reaction is stopped by addition, with stirring, of 100 cm³ of demineralized water. The aqueous phase is separated out by settling and the organic phase is washed again with 50 cm³ of demineralized water. The aqueous phase is separated out by settling and the organic phase is concentrated to dryness under reduced pressure. The solid is taken up in 400 cm³ of methyl isobutyl ketone and the product is extracted with twice 320 cm³ and then 80 cm³ of 0.2N sulphuric acid. The aqueous phases are combined and then extracted with 400 cm³ of dichloromethane. The organic phase is separated out by settling, concentrated to dryness under reduced pressure (30 kPa) at 30° C. and then dried under reduced pressure (150 Pa) at 40° C. to give 12.5 g of a white solid containing 72% (9 g) of pristinamycin $I_B$ and 5.6% (0.7 g) of pristinamycin $I_A$. Conversion yield: 84.9%.

EXAMPLE 3

540 g of crude pristinamycin I (pristinamycin $I_A$ 433 g, pristinamycin $I_B$ 25 g, pristinamycin $I_C$ 16 g, pristinamycin $I_D$ 19 g) are placed in solution, in a three-necked flask, in a mixture of 1460 cm³ of dichloromethane, 500 cm³ of acetic acid and 40 cm³ of ethylene glycol. 97.5 g of tetra-n-butylammonium periodate are added, while maintaining the temperature at 30° C. After stirring for 3 hours at 30° C., the reaction is stopped by addition, with stirring, of 2000 cm³ of demineralized water containing 34.7 g of hydroxylamine hydrochloride. The aqueous phase is settled and then separated out. The organic phase is washed with 2000 cm³ of water. After settling and separation, the organic phase is concentrated to a syrup. 2500 cm³ of ethyl acetate are poured onto this concentrate and the solution is then concentrated to a final volume of 1300 cm³. The suspension is filtered at 5° C. The crystals are washed with 3 times 400 cm³ of fresh ethyl acetate and dried at 40° C. under 1500 Pa of residual pressure. 331 g of a white product giving a pristinamycin IB assay of 91% are thus obtained.

EXAMPLE 4

180 g of crude pristinamycin I (containing 111.1 g of pristinamycin IA and 35.6 g of pristinamycin IB) are placed in solution, in a three-necked flask, in a mixture of 444 cm³ of dichloromethane, 128 cm³ of acetic acid and 10 cm³ of ethylene glycol. 25.9 g of tetra-n-butylammonium periodate are added. After stirring for 4 hours at 32° C., the reaction is stopped by addition, with stirring, of 1100 cm³ of tap water. The two phases are settled and separated. The organic phase is washed again 4 times in succession with, on each occasion, 1400 cm³ of tap water. The pH of these four washes is readjusted downwards with 5 ml of normal hydrochloric acid to facilitate the settlings. These four washes, settlings and separations are carried out at 35° C. The organic phase is concentrated by a factor of about two. 600 cm³ of ethyl acetate are gradually poured onto this concentrate, the crystallization being initiated after about one-third has been added. After the addition, supplying with ethyl acetate is continued with concomitant distillation, so as to keep a constant volume in the flask, i.e. about 600 cm³. After distillation to constant volume of about 800 cm³, the suspension is cooled to 0° C. and filtered. The filter cake is washed with twice 125 cm³ of ethyl acetate at 0° C. and dried under reduced pressure (1.5 kPa) at 40° C. to constant weight. 120 g of a light beige product containing 110 g of pristinamycin IB are obtained.

We claim:

1. A process for preparing a streptogramin of formula (I):

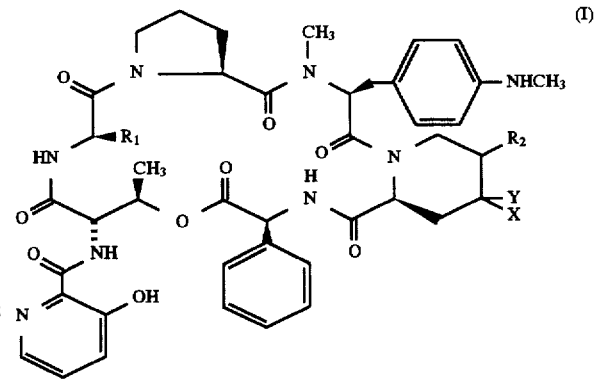

in which:

either $R_1$ represents a methyl or ethyl group, $R_2$ represents a hydrogen atom, and X and Y together form an oxo radical, or $R_1$ represents an ethyl radical, $R_2$ and X represent a hydrogen atom and Y represents a hydrogen atom or a hydroxyl radical, or $R_1$ represents an ethyl radical, $R_2$ represents a hydroxyl radical and X and Y together form an oxo radical, said process comprising demethylating a synergistin derivative of formula (II):

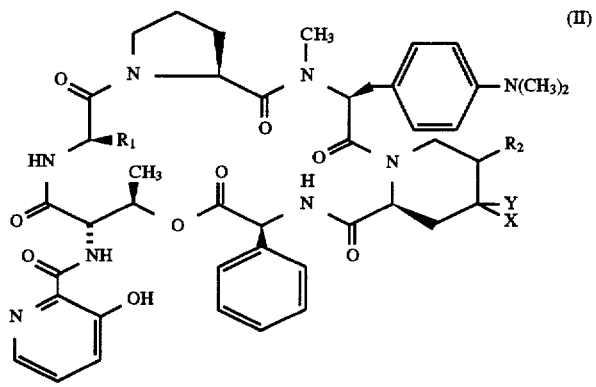

(II)

in which $R_1$, $R_2$, X and Y are as defined above, by treating said derivative with a periodate in acetic medium, followed by treating the product of said first treating step in an aqueous medium to release formaldehyde.

2. A process according to claim 1, wherein said periodate is tetra-n-butylammonium periodate or an alkaline periodate.

3. A process according to claim 2, wherein said alkaline periodate is sodium periodate.

4. A process according to claim 1, wherein said formaldehyde releasing treatment is a hydrolysis in either a homogeneous medium to which is added a strong acid or an acidic or non-acidic two-phase medium.

5. A process according to claim 2, said process further comprising adding, during the formaldehyde releasing treatment, an agent capable of consuming the formaldehyde in situ, wherein said agent is hydroxylamine, a bisulphite or hydrogen peroxide.

6. A streptogramin derivative, said streptogramin derivative having the formula:

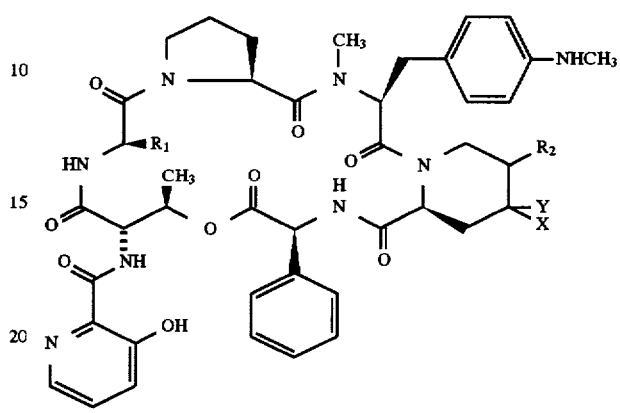

in which $R_1$ represents an ethyl radical, $R_2$ and X represent a hydrogen atom and Y represents a hydrogen atom or a hydroxyl radical.

* * * * *

UNITED STATES PATENT AND TRADEMARK OFFICE
CERTIFICATE OF CORRECTION

PATENT NO. : 5,789,537
DATED : August 4, 1998
INVENTOR(S) : Jean-Claude Barriere et al.

It is certified that error appears in the above-identified patent and that said Letters Patent is hereby corrected as shown below:

Claim 5, Column 5, Line 30, "claim 2" should read --claim 1--.

Signed and Sealed this

Fourteenth Day of September, 1999

Attest:

Q. TODD DICKINSON

*Attesting Officer*      *Acting Commissioner of Patents and Trademarks*